(12) United States Patent
Breuel et al.

(10) Patent No.: US 10,994,065 B2
(45) Date of Patent: May 4, 2021

(54) APPARATUS FOR CARRYING OUT AN EXTRACORPOREAL BLOOD TREATMENT AND METHOD FOR ADDING A SUBSTITUTION FLUID

(71) Applicant: FRESENIUS MEDICAL CARE DEUTSCHLAND GMBH, Bad Homburg (DE)

(72) Inventors: Lars Breuel, Witzleben/OT Achelstaedt (DE); Juergen Klewinghaus, Oberursel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 378 days.

(21) Appl. No.: 16/070,373

(22) PCT Filed: Jan. 5, 2017

(86) PCT No.: PCT/EP2017/000008
§ 371 (c)(1),
(2) Date: Jul. 16, 2018

(87) PCT Pub. No.: WO2017/121632
PCT Pub. Date: Jul. 20, 2017

(65) Prior Publication Data
US 2019/0022298 A1    Jan. 24, 2019

(30) Foreign Application Priority Data
Jan. 15, 2016 (DE) .................... 10 2016 000 367.7

(51) Int. Cl.
*A61M 1/34* (2006.01)
*A61M 1/36* (2006.01)
*A61M 1/10* (2006.01)

(52) U.S. Cl.
CPC .......... *A61M 1/342* (2013.01); *A61M 1/1006* (2014.02); *A61M 1/3621* (2013.01); *A61M 1/3496* (2013.01)

(58) Field of Classification Search
CPC .. A61M 1/1006; A61M 1/3437; A61M 1/342; A61M 1/3496; A61M 1/3621
See application file for complete search history.

(56) References Cited

U.S. PATENT DOCUMENTS

| 2005/0011833 A1* | 1/2005 | Stahl ................... A61M 1/1613 210/646 |
| 2005/0209563 A1 | 9/2005 | Hopping et al. |

(Continued)

FOREIGN PATENT DOCUMENTS

DE    102013014751    3/2015

*Primary Examiner* — Ariana Zimbouski
(74) *Attorney, Agent, or Firm* — Jacobson Holman PLLC

(57) ABSTRACT

The invention relates to an apparatus for carrying out an extracorporeal blood treatment in which a substitution fluid is administered to the patient, wherein the apparatus comprises an extracorporeal blood circuit and a substitution line opening into the extracorporeal blood circuit, wherein the substitution line has a pump for conveying substitution fluid into the extracorporeal circuit, wherein at least two, and preferably more than two, containers for the provision of a substitution fluid are connected separately and at the intake side of the pump to the substitution line, and wherein at least one pressure valve is arranged between the pump and at least one of the containers, said pressure valve allowing a flow of substitution fluid to the pump on an exceeding of an opening pressure.

12 Claims, 3 Drawing Sheets

(56) References Cited

U.S. PATENT DOCUMENTS

Figure 1:
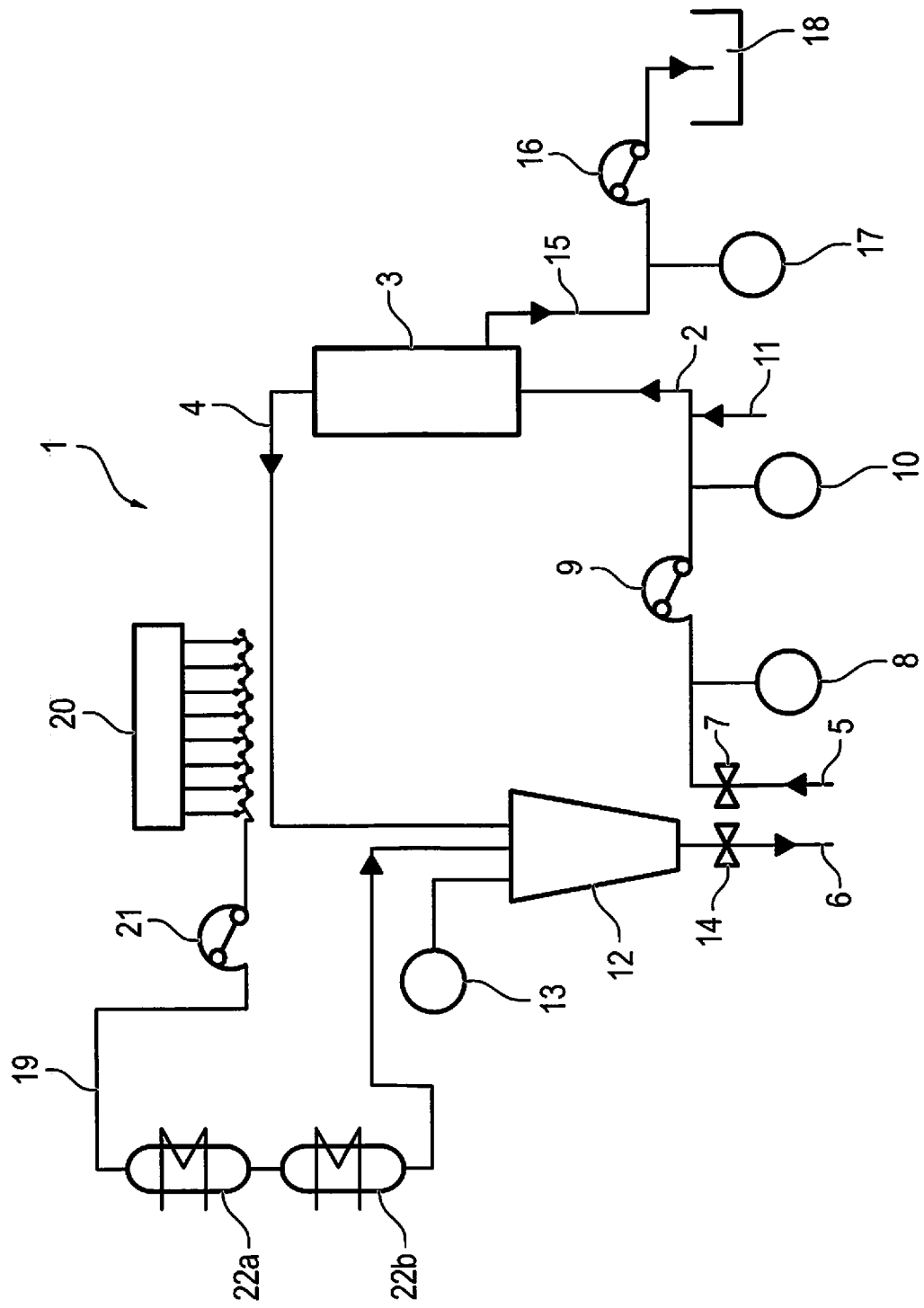

| | | | |
|---|---|---|---|
| 2007/0278155 A1* | 12/2007 | Lo | A61M 1/166 210/646 |
| 2009/0124963 A1* | 5/2009 | Hogard | A61M 1/14 604/30 |
| 2011/0106047 A1* | 5/2011 | Burbank | A61M 5/162 604/500 |
| 2013/0233394 A1 | 9/2013 | Nguyen et al. | |
| 2013/0248450 A1* | 9/2013 | Kenley | A61M 1/3633 210/650 |

* cited by examiner

APPARATUS FOR CARRYING OUT AN EXTRACORPOREAL BLOOD TREATMENT AND METHOD FOR ADDING A SUBSTITUTION FLUID

The invention, relates to an apparatus for carrying out an extracorporeal blood treatment in which a substitution fluid is administered to the patient.

The invention furthermore relates to a method for adding a substitution fluid.

In plasmapheresis, plasma is removed from the blood of a patient using a filter arranged in an extracorporeal blood circuit. The method is used, for example, for the treatment of some autoimmune diseases. In a variant of the method which is called plasma exchange, the removed plasma is discarded and a substitution fluid is introduced into the extracorporeal blood circuit. The substitution fluid can, for example, be a donor plasma.

The invention is, however, not restricted to plasmapheresis, but can rather generally be applied to devices for extracorporeal blood treatment in which a non-endogenous substitution fluid is supplied to the patient.

The substitution fluid is typically provided in a plurality of separate containers such as pouches which are separately connected to a substitution line. It is customary in this respect only to open the fluid communication between the container and the substitution line when the preceding container is empty. Any incompatibility reactions of the patient can thus be associated with the content of a specific container (for example with the plasma of a specific donor).

It is disadvantageous in known apparatus in this respect that the fluid connection has to be opened manually for every single container, which is laborious, time-intensive and personnel-intensive. It additionally means a user intervention at a point in time not to be determined exactly.

It is the object of the invention to provide an apparatus of the category in which these disadvantages are avoided.

Against this background, the invention relates to an apparatus for carrying out an extracorporeal blood treatment in which a substitution fluid is administered to the patient, wherein the apparatus comprises an extracorporeal blood circuit and a substitution line opening into the extracorporeal blood circuit, wherein the substitution line has a pump for conveying substitution fluid into the extracorporeal blood circuit, and wherein at least two, and preferably more than two, containers for providing a substitution fluid are connected separately and at the intake side of the pump to the substitution line. Provision is made in accordance with the invention that a pressure valve is arranged between the pump and at least one of the containers, said pressure valve allowing a flow of substitution fluid to the pump on an exceeding of an opening pressure.

The apparatus preferably serves the carrying out of a plasmapheresis treatment. The substitution fluid can, for example, be a donor plasma.

In an embodiment, the arrangement of the pressure valves and containers is such that a staggering of the opening pressures is achieved which have to be exerted by the pump to obtain substitution fluid from different containers. Since the containers are arranged at the intake side of the pump, a vacuum is generated by the pump downstream of the valves and the opening pressure results from the pressure difference between the normal pressure upstream of the valve and the vacuum downstream of the valves.

The pump first obtains substitution fluid from the container between which and the pump either no valve, the valve having the lowest opening pressure or the lowest number of identical valves is/are arranged. If this container has been emptied, the pump then obtains substitution fluid from the container between which and the pump the valve having the second-lowest opening pressure or the second-smallest number of identical valves is arranged. This continues until all the containers required for the treatment have been sequentially emptied.

In an embodiment, the pressure valves are arranged upstream of the connectors of the respective containers to the substitution line.

In an embodiment, at least one separate pressure valve is associated with each container. Alternatively, for example, a pressure valve may not be associated with one of the containers, i.e. a pressure valve can be associated with all of the containers except one.

In an embodiment, a different number of pressure valves connected in series is associated with different containers. These pressure valves connected in series can all have the same opening pressure in an embodiment. The opening pressure of the valves connected in series is summed. A staggering of the opening pressures is thus achieved despite the use of identical valves.

In an alternative embodiment, pressure valves having different opening pressures are associated with different containers. A staggering of the opening pressures can also be achieved in this manner.

Mixed forms are also conceivable, for example the use of two or more different pressure valves having different opening pressures and the arrangement of these pressure valves in series for achieving an opening pressure which is higher than the opening pressure of that individual valve having the highest opening pressure.

In an embodiment, some or all of the containers are connected in parallel to the substitution line.

In an alternative embodiment, some or all of the containers are connected in series to the substitution line. Provision can be made with a connection in series that the required opening pressures increase as the distance of the containers from the pump increases.

Mixed forms are also conceivable, for example two or more strands which are connected in parallel and to which the containers are connected in series.

With a connection of the containers to the substitution line in series, the pressure valves are arranged in an embodiment between the connectors of the containers to the substitution line. Pressure valves are preferably arranged between all the connectors. In this embodiment, the required opening pressures are summed for the access to those containers between which and the pump a plurality of pressure valves are disposed in the substitution line. This embodiment has the advantage that the apparatus can optionally make do with fewer pressure valves.

In an embodiment, no pressure valve is arranged between the pump and the first container of the series. That container is understood as the first container whose connector to the substitution line is closer to the pump than the connectors of all the other containers. Alternatively, a pressure valve can also be arranged between the first container of the series and the pump.

In an embodiment, all the pressure valves have the same opening pressure. This can be the case in all the aforesaid embodiments. A cost saving hereby results by the use of identical parts.

In an embodiment, the pressure valves are check valves which only allow a flow of substitution fluid in the direction of the pump.

In an embodiment, the containers are compressible. They are preferably plastic pouches. In this case, the pouch volume can reduce as the contained fluid volume reduces on the sucking empty by the pump.

As regards the magnitude of the opening pressure, provision can thus be made, for example, that the opening pressure of individual valves is between 20 and 300 mbar, and preferably between 50 and 100 mbar.

It is further intended within the framework of the present invention to provide a method for extracorporeal blood treatment using an apparatus in accordance with the invention, wherein substitution fluid is administered into the extracorporeal blood circuit or into a substitution line in fluid communication therewith, and wherein the substitution fluid is sequentially conveyed from the different containers of the apparatus such that the conveying from one container only begins when the preceding container is empty.

Figure 2:
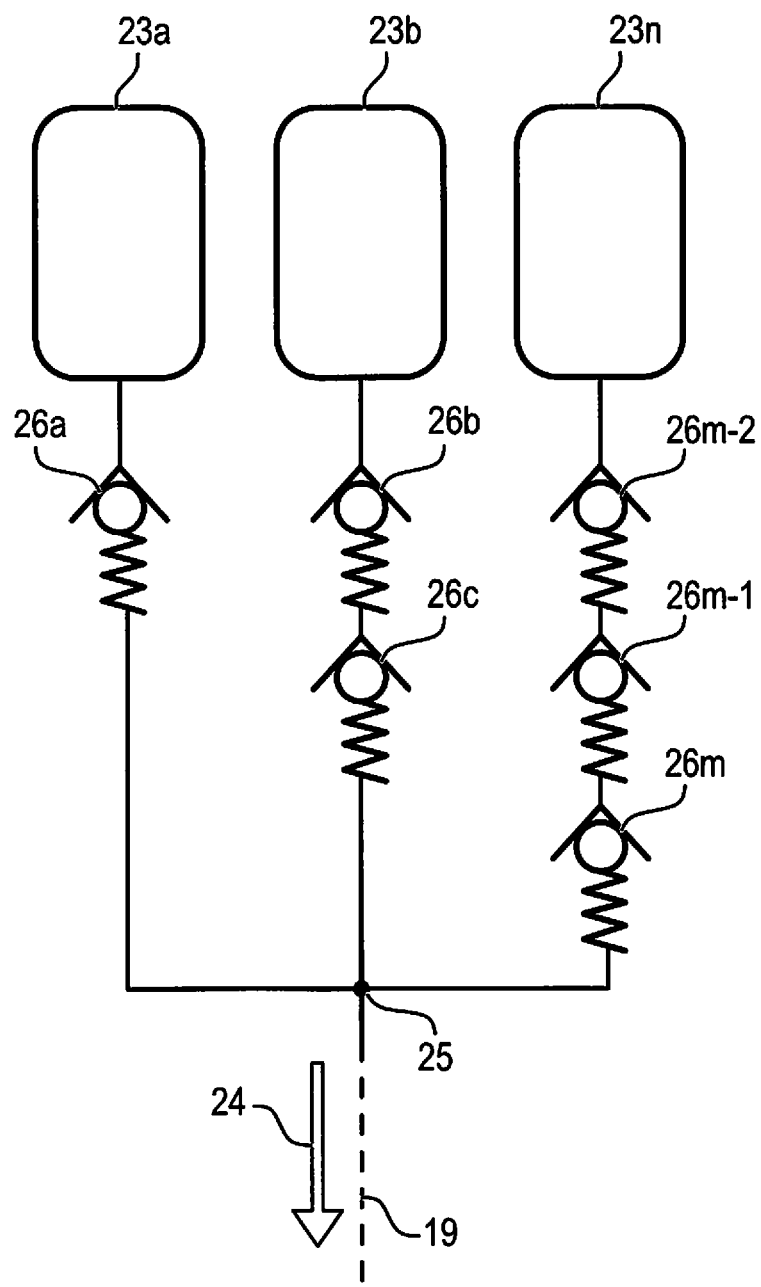
Figure 3:
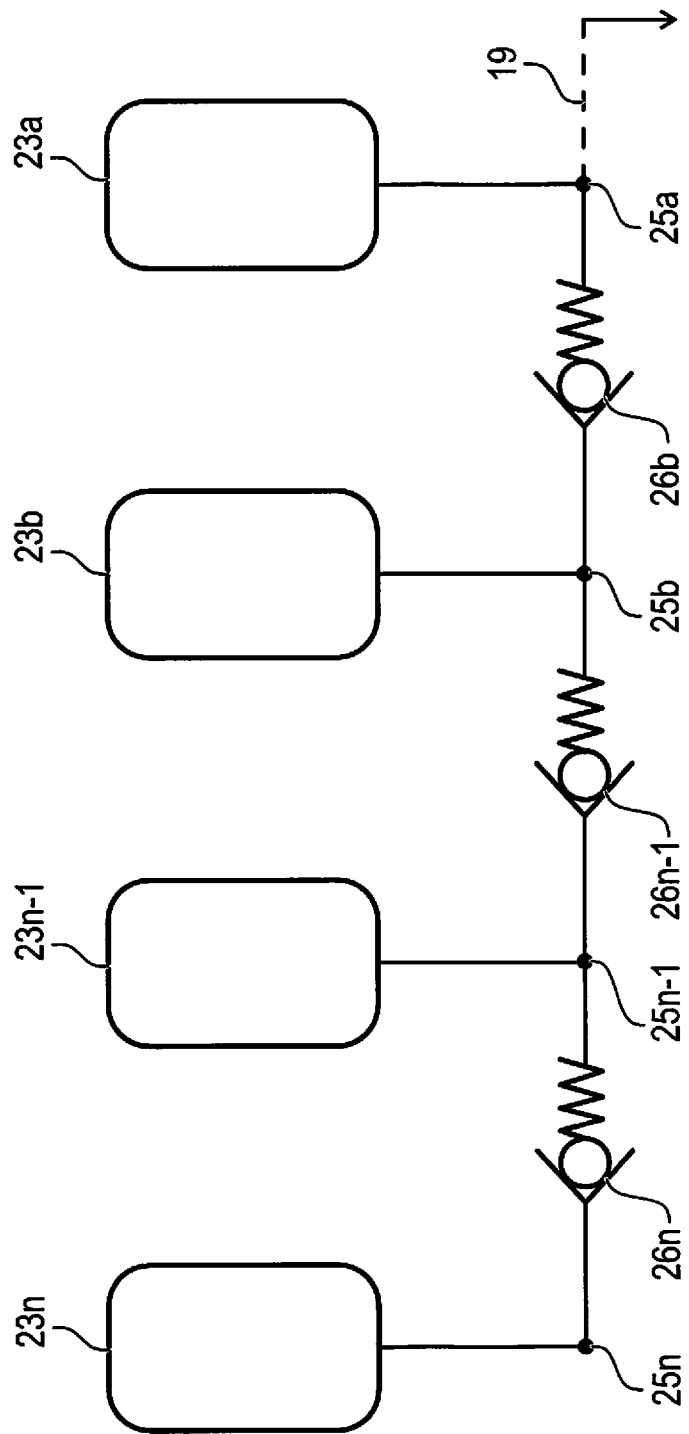

Further details and advantages of the invention result from the embodiments explained in the following with reference to the Figures. There are shown in the Figures:

FIG. 1: a flow diagram of an apparatus for plasma exchange;

FIG. 2: an embodiment of the apparatus in accordance with the invention with a parallel arrangement of the containers; and FIG. 3: an embodiment of the apparatus in accordance with the invention with an arrangement of the containers in series.

The extracorporeal blood circuit shown schematically in FIG. 1 of an embodiment of an apparatus in accordance with the invention is marked by the reference numeral 1.

It comprises an arterial line 2, a plasma filter 3 and a venous line 4. An arterial port 5 is arranged at the lead side of the arterial line 2 and a venous port 6 is arranged at the return side of the venous line 4. These ports 5 and 6, which may be needles, for example, serve the connection of the apparatus to a patient.

An arterial clamp 7, a pressure sensor 8 for measuring the arterial pressure, a blood pump 9, a further pressure sensor 10 for measuring the pump pressure, and a line 11 for supplying an anticoagulant such as heparin are arranged staggered in the direction of flow in the arterial line 2.

A drop chamber 12, a pressure sensor 13 for measuring the venous pressure and a venous clamp 14 are located in the venous line 4.

The plasma filter 3 comprises a semipermeable membrane which separates the extracorporeal blood circuit 1 from a drainage system 15 for plasma separated from the blood. The drainage system 15 comprises a filtration pump 16, a pressure sensor 17 for measuring the filtration pressure and a drain 18 for collecting or disposing of the separated plasma.

The apparatus furthermore comprises a substitution line 19 which opens into the venous line 4 of the extracorporeal blood circuit 1 upstream of the drop chamber 12 or at the drop chamber 12. A supply system 20 for substitution fluid, to which the core idea of the present invention relates, is arranged upstream of the substitution line 19 and will be discussed in detail in the following with reference to FIGS. 2 and 3. A substitution pump 21 which serves the conveying of substitution fluid from the system 20 into the venous line 4 is furthermore arranged in the substitution line 19. The substitution line 19 furthermore comprises heating pouches 22a and 22b which comprise a heat exchanger and which serve to raise the temperature of the substitution fluid to body temperature.

An embodiment of a supply system 20 for substitution fluid configured in accordance with the invention is shown in FIG. 2. The supply system 20 shown has a plurality of plastic pouches 23a-n which are filled with substitution fluid such as donor plasma. Three pouches are shown in the Figure, but the explained principle can be used on systems having any desired number of pouches. The pouches 23a-n are connected to the substitution line 19 upstream of the pump 21. They are connected in parallel and open into the substitution line 19 at a common connector 25. The direction of flow for substitution fluid in the substitution line 19 is shown with reference to the arrow 24. At least one check valve 26 is arranged between each of the pouches 23a-n and the connector 25 in the fluid channel. These valves 26a-m are each configured such that a flow of substitution fluid from the pouches 23 into the substitution line 19 is made possible on reaching a certain opening pressure. A flow in the opposite direction is not possible. All of the valves 26 are of identical design in the Figure and also open on a reaching of the same opening pressure in this respect. If a plurality of pressure valves 26 are arranged in series between a specific plastic pouch 23n and the connector 25, the opening pressures of these valves arranged in series are summed to a total opening pressure for a specific pouch. In the example shown, the lowest total opening pressure is required for emptying the pouch 23a since only one valve 26a is arranged between this pouch and the connector 25.

If therefore the substitution medium pump 21 is operated, it generates a vacuum downstream of the valves 26 so that the valve 26a opens on reaching a specific pressure difference and substitution fluid can move out of the pouch 23a into the substitution line 19 and can be conveyed into the extracorporeal blood circuit 1. No substitution solution is taken out of the pouches 23b-n as long as the pouch 23a is not completely emptied. Once the pouch 23a is completely empty, the vacuum downstream of the valves 26 automatically increases on a continuous operation of the pump 21 until the pressure difference corresponds to the total opening pressure of the valves 26b and 26c. These valves 26b and 26c then open and substitution fluid can move out of the pouch 23b into the substitution line 19 and can be conveyed into the extracorporeal blood circuit 1. This principle is repeated accordingly for the further pouches 23n and valves 26m.

Provision can be made in a variant not to arrange any valve at all in the line between one of the pouches, for example the pouch 23a, and the connector 25. Substitution fluid can thus already be taken from this bag without any differential pressure.

Provision can furthermore be made in an alternative embodiment to use two or more different valves 26 and so to reduce the total number of valves 26 required. For example, only one valve, whose opening pressure is higher than the opening pressure of the valve 23a, can then be arranged between the pouch 23b and the connector 25.

If two different valves are to be used, with a first valve having an opening pressure of 50 mbar and a second valve having an opening pressure of 100 mbar, the configuration shown in Table 1 is conceivable, for example:

TABLE 1

| Pouch connector (n) | Valve 1 | Valve 2 | Total opening pressure [mbar] |
|---|---|---|---|
| 1 | 0 | 0 | 0 |
| 2 | 1 | 0 | 50 |

TABLE 1-continued

| Pouch connector (n) | Valve 1 | Valve 2 | Total opening pressure [mbar] |
|---|---|---|---|
| 3 | 0 | 1 | 100 |
| 4 | 1 | 1 | 150 |
| 5 | 0 | 2 | 200 |
| etc. | | | |

A further embodiment of a supply system 20 in accordance with the present invention is shown in FIG. 3, with the pouches 23*a-an* being connected to the substitution line 19 in series so that the connectors 25*a-n* are disposed after one another in series at the substitution line 19. Respective valves 26*b-n* are arranged between the connectors 25*a-n*, with them in this respect preferably being valves which are of identical design and which in this respect also all open on reaching the same opening pressure.

If a substitution medium pump 21 is operated in this embodiment, the first pouch 21*a* is first emptied between which and the pump no valve 26 is located. Once this pouch is completely empty, the pump 21 generates a vacuum downstream of the first valve 26*b* so that it opens on reaching a specific pressure difference (for example 50 mbar) and substitution fluid can move out of the second pouch 23*b* into the substitution line 19 and can be conveyed into the blood circuit 1. No substitution solution is still removed from the pouches 23*c-n* since a higher pressure difference would be necessary in order also to open the second valve 26*c* in addition to the first valve 26*b*. If now the pouch 23*b* is also completely empty, the vacuum increases on a continuous operation of the pump 21 until the pressure difference corresponds to the total opening pressure of the valves 26*b* and 26*c*. The valve 26*c* then opens and substitution fluid can move out of the pouch 23*c* into the substitution line 19 and can be conveyed into the extracorporeal, blood circuit 1. This principle is repeated accordingly for the further pouches 23*n* and valves 26*n*.

It is advantageous in the embodiment in accordance with FIG. 3 that the number of required valves is reduced and at the same time the risk is reduced that two pouches are emptied simultaneously since the opening pressures of the valves do not have to be exactly matched to one another.

The invention claimed is:

1. An apparatus for carrying out an extracorporeal blood treatment in which a substitution fluid is administered to a patient, wherein the apparatus comprises an extracorporeal blood circuit and a substitution line opening into the extracorporeal blood circuit, wherein the substitution line has a pump for conveying substitution fluid into the extracorporeal blood circuit, and wherein containers for providing a substitution fluid are connected separately by connectors, respectively, and at an intake side of the pump to the substitution line, characterized in that
at least one pressure valve is arranged between the pump and at least one of the containers, said at least one pressure valve allowing a flow of substitution fluid to the pump on an exceeding of an opening pressure and the arrangement of the at least one pressure valve and the at least one of the containers is such that a staggering of the opening pressure is achieved which has to be exerted by the pump to obtain substitution fluid from the containers.

2. The apparatus in accordance with claim 1, characterized in that the at least one pressure valve is arranged upstream of the separate connectors of the containers, respectively, to the substitution line.

3. The apparatus in accordance with claim 2, characterized in that the at least one pressure valve is associated with each container, respectively.

4. The apparatus in accordance with claim 2, characterized in that different numbers of the at least one pressure valve connected in series are associated with the containers, respectively.

5. The apparatus in accordance with claim 2, characterized in that different pressure valves of the at least one pressure valve having different opening pressures are associated with the containers, respectively.

6. The apparatus in accordance with claim 1, characterized in that some or all of the containers are connected to the substitution line in parallel.

7. The apparatus in accordance with claim 1, characterized in that some or all of the containers are connected to the substitution line in series.

8. An apparatus in accordance with claim 7, characterized in that the at least one pressure valve is arranged in the substitution line between the connectors of the containers to the substitution line.

9. An apparatus in accordance with claim 8, characterized in that no pressure valve is arranged between the pump and a first container of the series; and/or in that all pressure valves of the at least one pressure valve have the same opening pressure.

10. A method for adding a substitution fluid into an extracorporeal blood circuit using the apparatus in accordance with claim 1, wherein the substitution fluid is conveyed sequentially out of the containers of the apparatus such that the conveying from one container only begins when the preceding container is emptied.

11. The apparatus in accordance with claim 1 comprising more than two of the containers.

12. The apparatus in accordance with claim 4, characterized in that the different numbers of the at least one pressure valve all have the same opening pressure.

* * * * *